US007494975B2

(12) United States Patent
Vives et al.

(10) Patent No.: US 7,494,975 B2
(45) Date of Patent: Feb. 24, 2009

(54) ANTI-HIV COMPOSITION, PRODUCTION METHOD THEREOF AND MEDICAMENT

(75) Inventors: Romain Vives, La Riviere (FR); Quentin Sattentau, Oxford (GB); Claudio Vita, Gif sur Yvette (FR); Hugues Lortat-Jacob, Saint Ismier (FR)

(73) Assignees: Commissariat a l'Energie Atomique, Paris (FR); Centre National de la Recherche Scientifique, Paris (FR)

( * ) Notice: Subject to any disclaimer, the term of this patent is extended or adjusted under 35 U.S.C. 154(b) by 427 days.

(21) Appl. No.: 10/509,686

(22) PCT Filed: Apr. 17, 2003

(86) PCT No.: PCT/FR03/01234

§ 371 (c)(1),
(2), (4) Date: Oct. 12, 2004

(87) PCT Pub. No.: WO03/089000

PCT Pub. Date: Oct. 30, 2003

(65) Prior Publication Data

US 2006/0084593 A1    Apr. 20, 2006

(30) Foreign Application Priority Data

Apr. 19, 2002    (FR) .................................. 02 04926

(51) Int. Cl.
*A61K 38/16*    (2006.01)
*C07K 1/00*    (2006.01)
*C07K 14/00*    (2006.01)
*C07K 17/00*    (2006.01)
*C08B 37/10*    (2006.01)

(52) U.S. Cl. .............................. 514/8; 530/395; 536/21
(58) Field of Classification Search ....................... None
See application file for complete search history.

(56) References Cited

U.S. PATENT DOCUMENTS

2006/0121538 A1 * 6/2006 Vita et al. .................. 435/7.23

FOREIGN PATENT DOCUMENTS

| EP | 0 249 390 |      | 12/1987 |
|----|-----------|------|---------|
| EP | 0 332 952 |      | 9/1989  |
| EP | 0 355 905 | A1 * | 9/1989  |
| WO | 92 04909  |      | 4/1992  |
| WO | 02 059146 |      | 8/2002  |

OTHER PUBLICATIONS http://redppoll.pharmacy.ualberta.ca/drugbank/cgi-bin/getCard.cgi?CARD=APRD00068.txt, accessed online Jan. 5, 2008, pp. 1-3.*
Dowd et al. B-Turn Phe n HIV-1 Env Binding Site of CD4 and CD4 Mimetic Miniprotein Enhances Env Binding Affinity but is Not Required for Activation of C0-Receptor/17b Site. Biochemistry. Jun. 4, 2002. vol. 41, pp. 7038-7046.*
Martin et al. Engineering Novel Bioactive Mini-Proteins on Natrual Scaffolds. Tetrahedron 2000. vol. 56, pp. 9451-9460.*
Witvrouw, M. et al. "Sulfated Polysaccharides Extracted from Sea Algae as Potential Antiviral Drugs", Gen. Pharmac., vol. 29, No. 4, pp. 497-511, XP002056013 1997.
Moulard, Maxime et al. "Selective Interactions of Polyanions with Bases Surfaces on Human Immunodeficiency Virus Type 1 gp120", Journal of Virology, vol. 74, No. 4, pp. 1948-1960, XP002226781 2000.
Sullivan, Nancy et al. "Determinants of Human Immunodeficiency Virus Type 1 Envelope Glycoprotein Activation by Soluble CD4 and Monoclonal Antibodies", Journal of Virology, vol. 72, No. 8, pp. 6332-6338, XP002226782 1998.
Harrop, Hilary A. et al. "Heparin specifically inhibits binding of V3 loop antibodies to HIV-1 gp120, an effect potentiated by CD4 binding", AIDS, vol. 8, No. 2, pp. 183-192, XP002226783 1994.
Chan, David C. et al. "HIV Entry and Its Inhibition", Cell, vol. 93, pp. 681-684 1998.
Clapham, Paul R. "HIV and chemokines: ligands sharing cell-surface receptors", Trends in Cell Biology, vol. 7, pp. 264-268 1997.
Michael, Nelson L. et al. "HIV-1 entry inhibitors: Evading the issue", Nature Medicine, vol. 5, No. 7, pp. 740-742 1999.
Chan, David C. et al. "Evidence that a prominent cavity in the coiled coil of HIV type 1 gp41 is an attractive drug target", Proc. Natl. Acad. Sci. vol. 95, pp. 15613-15617 1998.
Doms, Robert W. et al. "HIV-1 Membrane Fusion: Targets of Opportunity", The Journal of Cell Biology, vol. 151, No. 2, pp. F9-F13 2000.
Schenten, Dominik et al. "Effects of Soluble CD4 on Simian Immunodeficiency Virus Infection of CD4-Positive and CD4-Negative Cells", Journal of Virology, vol. 73, No. 7, pp. 5373-5380 1999.
Chen, Ji-Dai et al. "Inactivation of HIV-1 chemokine co-receptor CXCR-4 by a novel intrakine strategy", Nature Medicine, vol. 3, No. 10, pp. 1110-1116 1997.
Oberlin, Estelle et al. "The CXC chemokine SDF-1 is the ligand for LESTR/fusin and prevents infection by T-cell-line-adapted HIV-1", Nature, vol. 382, pp. 833-835 1996.
Proudfoot, Amanda et al. "Chemokine Receptors—Future Therapeutic Targets for HIV?" Biochemical Pharmacology, vol. 57, pp. 451-463 1999.
Murakami, Tsutomu et al. "A Small Molecule CXCR4 Inhibitor that Blocks T Cell Line-tropic HIV-1 Infection", J. Exp. Med., vol. 186, No. 8, pp. 1389-1393 1997.

(Continued)

*Primary Examiner*—Cecilia Tsang
*Assistant Examiner*—Marcela M Cordero Garcia
(74) *Attorney, Agent, or Firm*—Oblon, Spivak, McClelland, Maier & Neustadt, P.C.

(57) ABSTRACT

The present invention relates to an anti-HIV composition and to the method for producing it.

The composition of the present invention comprises a polyanion and a molecule capable of inducing the exposure of the CD4i epitope of the gp120 viral protein. The polyanion may be chosen, for example, from the group consisting of heparin, heparan sulphate, and a polyanion equivalent to heparin or to heparan sulphate. The molecule capable of inducing the exposure of the CD4i epitope of the gp120 viral protein is a CD4 peptide or a derivative thereof.

The present invention also relates to the use of said composition for producing a medicinal product, in particular a medicinal product intended for the treatment of AIDS.

7 Claims, 6 Drawing Sheets

OTHER PUBLICATIONS

Mondor, Isabelle et al. "Human Immunodeficiency Virus Type 1 Attachment to HeLa CD4 Cells is CD4 Independent and gp120 Dependent and Requires Cell Surface Heparans", Journal of Virology, vol. 72, No. 5, pp. 3623-3634 1998.

Roderiquez, Gregory et al. "Mediation of Human Immunodeficiency Virus Type 1 Binding by Interaction of Cell Surface Heparan Sulfate Proteoglycans with the V3 Region of Envelope gp120-gp41", Journal of Virology, vol. 69, No. 4, pp. 2233-2239 1995.

Abrams, Donald I. et al. "Oral Dextran Sulfate (UA001) in the Treatment of the Acquired Immunodeficiency Syndrome (AIDS) and AIDS-Related Complex", Annals of Internal Medicine, vol. 110, No. 3, pp. 183-188 1989.

Flexner, Charles et al. "Pharmacokinetics, Toxicity, and Activity of Intravenous Dextran Sulfate in Human Immunodeficiency Virus Infection", Antimicrobial Agents and Chemotherapy, vol. 35, No. 12, pp. 2544-2550 1991.

Chernyak, Anatoly et al. "Conjugating oligosaccharides to proteins by squaric acid diester chemistry: rapid monitoring of the progress of conjugation, and recovery of the unused ligand", Carbohydrate Research, vol. 330, pp. 479-486 2001.

Kuberan, B. et al. "Preparation and isolation of neoglycoconjugates using biotin-streptavidin complexes", Glycoconjugate Journal, vol. 16, pp. 271-281 1999.

Najjam, Saloua et al. "Characterization of Human Recombinant Interleukin 2 Binding to Heparin and Heparan Sulfate Using an Elisa Approach", Cytokine, vol. 9, No. 12, pp. 1013-1022 1997.

Dreef-Tromp, C.M. et al. "Biological Properties of Synthetic Glycoconjugate Mimics of Heparin Comprising Different Molecular Spacers", Bioorganic and Medicinal Chemistry Letters, vol. 8, pp. 2081-2086 1998.

Grootenhuis, P.D. et al. "Rational Design of Synthetic heparin analogues with tailor-made coagulation factor inhibitory activity", Nature Structural Biology, vol. 2, No. 9, pp. 736-739 1995.

Claudio Vita et al., "Rational engineering of a miniprotein that reproduces the core of the CD4 site interacting with HIV-1 envelope glycoprotein", PNAS. Nov. 9, 1999, vol. 96, No. 23, pp. 13091-13096.

Loïc Martin et al., "Rational design of a CD4 mimic that inhibits HIV-1 entry and exposes cryptic neutralization epitopes", www.nature.com/naturebiotechnology, Jan. 2003, vol. 21, pp. 71-76.

* cited by examiner

SEQUENCE LISTING

```
<160> NUMBER OF SEQ ID NOS: 18

<210> SEQ ID NO 1
<211> LENGTH: 16
<212> TYPE: PRT
<213> ORGANISM: Homo sapiens

<400> SEQUENCE: 1

Gln Ile Lys Ile Leu Gly Asn Gln Gly Ser Phe Leu Thr Lys Gly Pro
1               5                   10                  15

<210> SEQ ID NO 2
<211> LENGTH: 31
<212> TYPE: PRT
<213> ORGANISM: Scorpion

<400> SEQUENCE: 2

Ala Phe Cys Asn Leu Arg Met Cys Gln Leu Ser Cys Arg Ser Leu Gly
1               5                   10                  15

Leu Leu Gly Lys Cys Ile Gly Asp Lys Cys Glu Cys Val Lys His
            20                  25                  30

<210> SEQ ID NO 3
<211> LENGTH: 28
<212> TYPE: PRT
<213> ORGANISM: Artificial Sequence
<220> FEATURE:
<223> OTHER INFORMATION: Synthetic Peptide

<400> SEQUENCE: 3

Cys Asn Leu Ala Arg Cys Gln Leu Arg Cys Lys Ser Leu Gly Leu Leu
1               5                   10                  15

Gly Lys Cys Ala Gly Ser Phe Cys Ala Cys Gly Pro
            20                  25

<210> SEQ ID NO 4
<211> LENGTH: 28
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: X = Cys or thiopropionic acid

<400> SEQUENCE: 4

Xaa Asn Leu Ala Arg Cys Gln Leu Arg Cys Lys Ser Leu Gly Leu Leu
1               5                   10                  15
```

Gly Lys Cys Ala Gly Ser Phe Cys Ala Cys Gly Pro
            20                  25

<210> SEQ ID NO 5
<211> LENGTH: 27
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: X = Cys or thiopropionic acid
<220> FEATURE:
<221> NAME/KEY: MOD_RES
<222> LOCATION: (23)..(23)
<223> OTHER INFORMATION: X = bi-phenylalanin or naphtylalanin

<400> SEQUENCE: 5

Xaa Asn Leu His Phe Cys Val Gln Arg Cys His Ser Leu Gly Leu Leu
1               5                   10                  15

Gly Lys Cys Ala Gly Ser Xaa Cys Ala Cys Val
            20                  25

<210> SEQ ID NO 6
<211> LENGTH: 27
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: X = Cys or thiopropionic acid

<400> SEQUENCE: 6

Xaa Asn Leu Ala Phe Cys Gln Leu Arg Cys Lys Ser Leu Gly Leu Leu
1               5                   10                  15

Gly Lys Cys Ala Gly Ser Phe Cys Ala Cys Val
            20                  25

<210> SEQ ID NO 7
<211> LENGTH: 27
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: X = Cys or thiopropionic acid

<400> SEQUENCE: 7

Xaa Asn Leu Ala Phe Cys Gln Leu Arg Cys Lys Ser Leu Gly Leu Leu
1               5                   10                  15

Gly Lys Cys Ala Ser Ser Phe Cys Ala Cys Val
            20                  25

<210> SEQ ID NO 8
<211> LENGTH: 27
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: X = Cys or thiopropionic acid

```
<400> SEQUENCE: 8

Xaa Asn Leu Ala Phe Cys Gln Leu Arg Cys Lys Ser Leu Gly Leu Leu
1               5                   10                  15

Gly Lys Cys Ala Gly His Phe Cys Ala Cys Val
            20                  25

<210> SEQ ID NO 9
<211> LENGTH: 27
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: X = Cys or thiopropionic acid

<400> SEQUENCE: 9

Xaa Asn Leu Ala Phe Cys Gln Leu Arg Cys Lys Ser Leu Gly Leu Leu
1               5                   10                  15

Gly Lys Cys Ala Gly Asn Phe Cys Ala Cys Val
            20                  25

<210> SEQ ID NO 10
<211> LENGTH: 27
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: X = Cys or thiopropionic acid
<220> FEATURE:
<221> NAME/KEY: MOD_RES
<222> LOCATION: (23)..(23)
<223> OTHER INFORMATION: X = bi-phenylalanin or naphtylalanin

<400> SEQUENCE: 10

Xaa Asn Leu Gln Phe Cys Gln Leu Arg Cys Lys Ser Leu Gly Leu Leu
1               5                   10                  15

Gly Lys Cys Ala Gly Ser Xaa Cys Ala Cys Val
            20                  25

<210> SEQ ID NO 11
<211> LENGTH: 27
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: X = Cys or thiopropionic acid
<220> FEATURE:
<221> NAME/KEY: MOD_RES
<222> LOCATION: (23)..(23)
<223> OTHER INFORMATION: X = bi-phenylalanin or naphtylalanin

<400> SEQUENCE: 11

Xaa Asn Leu His Phe Cys Gln Leu Arg Cys Lys Ser Leu Gly Leu Leu
1               5                   10                  15

Gly Lys Cys Gln Gly Ser Xaa Cys Thr Cys Val
            20                  25

<210> SEQ ID NO 12
<211> LENGTH: 27
```

```
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: X = Cys or thiopropionic acid
<220> FEATURE:
<221> NAME/KEY: MOD_RES
<222> LOCATION: (23)..(23)
<223> OTHER INFORMATION: X = bi-phenylalanin or naphtylalanin

<400> SEQUENCE: 12

Xaa Asn Leu Ala Arg Cys Gln Leu Arg Cys Lys Ser Leu Gly Leu Leu
1               5                   10                  15

Gly Lys Cys Ala Gly Ser Xaa Cys Ala Cys Val
            20                  25

<210> SEQ ID NO 13
<211> LENGTH: 27
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: X = Cys or thiopropionic acid
<220> FEATURE:
<221> NAME/KEY: MOD_RES
<222> LOCATION: (23)..(23)
<223> OTHER INFORMATION: X = bi-phenylalanin or naphtylalanin

<400> SEQUENCE: 13

Xaa Asn Leu His Phe Cys Gln Leu Arg Cys Lys Ser Leu Gly Leu Leu
1               5                   10                  15

Gly Lys Cys Ala Gly Ser Xaa Cys Ala Cys Val
            20                  25

<210> SEQ ID NO 14
<211> LENGTH: 27
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: X = Cys or thiopropionic acid
<220> FEATURE:
<221> NAME/KEY: misc_feature
<222> LOCATION: (21)..(21)
<223> OTHER INFORMATION: Xaa can be any naturally occurring amino acid
<220> FEATURE:
<221> NAME/KEY: MOD_RES
<222> LOCATION: (23)..(23)
<223> OTHER INFORMATION: X = bi-phenylalanin or naphtylalanin

<400> SEQUENCE: 14

Xaa Asn Leu His Phe Cys Gln Leu Arg Cys Lys Ser Leu Gly Leu Leu
1               5                   10                  15

Gly Lys Cys Ala Xaa Ser Xaa Cys Ala Cys Ile
            20                  25

<210> SEQ ID NO 15
<211> LENGTH: 27
<212> TYPE: PRT
<213> ORGANISM: Artificial Sequence
<220> FEATURE:
```

```
<223> OTHER INFORMATION: Synthetic Peptide
<220> FEATURE:
<221> NAME/KEY: MISC_FEATURE
<222> LOCATION: (1)..(1)
<223> OTHER INFORMATION: X = Cys or thiopropionic acid

<400> SEQUENCE: 15

Xaa Asn Leu His Phe Cys Val Gln Arg Cys His Ser Leu Gly Lys Leu
1               5                   10                  15

Gly Lys Cys Ala Gly Ser Phe Cys Ala Cys Val
            20                  25

<210> SEQ ID NO 16
<211> LENGTH: 27
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: X = Cys or thiopropionic acid

<400> SEQUENCE: 16

Xaa Asn Leu His Phe Cys Val Gln Arg Cys His Ser Leu Gly Leu Lys
1               5                   10                  15

Gly Lys Cys Ala Gly Ser Phe Cys Ala Cys Val
            20                  25

<210> SEQ ID NO 17
<211> LENGTH: 27
<212> TYPE: PRT
<213> ORGANISM: Artificial Sequence
<220> FEATURE:
<223> OTHER INFORMATION: Synthetic Peptide

<400> SEQUENCE: 17

Cys Asn Leu Ala Arg Cys Gln Leu Ser Cys Lys Ser Leu Gly Leu Lys
1               5                   10                  15

Gly Gly Cys Gln Gly Ser Phe Cys Thr Cys Gly
            20                  25

<210> SEQ ID NO 18
<211> LENGTH: 33
<212> TYPE: PRT
<213> ORGANISM: Artificial Sequence
<220> FEATURE:
<223> OTHER INFORMATION: Synthetic Peptide

<400> SEQUENCE: 18

Val Ser Cys Thr Thr Ser Lys Glu Cys Trp Ser Val Cys Gln Arg Leu
1               5                   10                  15

His Asn Thr Ser Lys Gly Gly Cys Gln Gly Ser Phe Cys Thr Cys Gly
                20                  25                  30

Pro
```

ANTI-HIV COMPOSITION, PRODUCTION METHOD THEREOF AND MEDICAMENT

CROSS-REFERENCE TO RELATED APPLICATIONS

The present application is a 35 U.S.C. § 371 National Stage patent application of International patent application PCT/FR03/01234, filed on Apr. 17, 2003, which claims priority to French patent application FR 02/04926, filed on Apr. 19, 2002

TECHNICAL FIELD

The present invention relates to an anti-HIV composition and to the method for producing it. It also relates to the use of said composition for producing an anti-HIV medicinal product.

Entry of the human immunodeficiency virus (HIV) into the cell is an essential step in the viral infectious cycle. This process is divided up into two phases corresponding to the interaction of the virus at the cell surface at the level of specific receptors of the host, and to the penetration of the genetic material of the virus into the target cell.

Over the past ten years, the mechanisms of adhesion of HIV to the cell surface have become considerably clarified. The molecular partners involved are now well defined, as disclosed in documents [1, 2] of the reference list attached in the appendix.

As regards the virus, the envelope glycoproteins gp120 and gp41 constitute the "key to the vault" from the virus/cell interaction complex. Initially, g-120 associates with a transmembrane protein of the host cell, CD4. This interaction results in a conformational change in gp120, which will expose a particular epitope, referred to as "CD4-induced" epitope (CD4i). CD4i constitutes a binding site for certain members of the chemokine receptor family (mainly CXCR4 and CCR5), which will play a role of gp120 coreceptor at the cell surface. This second interaction, gp120/CCR5 or gp120/CXCR4, then results in a reorganization of the gp120/gp41 protein complex. This reorganization exposes gp41, which then allows initiation of the fusion of the cell and viral membranes, and entry of the viral genetic material into the cell.

These studies make it possible to define two novel therapeutic targets: inhibition of the interaction of gp120 with CD4 and CCR5 or CXCR4, and inhibition of the fusion [3].

PRIOR ART

The references between [ ] refer to the reference list attached in the appendix.

In the field of human immunodeficiency virus (HIV) infection, tritherapies associating nucleoside inhibitors, non-nucleoside inhibitors and/or antiproteases ("HAART" for "Highly Active Antiretroviral Treatment") target the replication and maturation of the virus.

These treatments make it possible to substantially reduce the viral load, but they do not make it possible to totally eradicate the virus from the body. In fact, if the taking of medicinal products is stopped, even after several years of treatment, this invariably results in a rapid increase again in the viral load in the plasma. Besides this disadvantage, these treatments are considerably toxic and have many side effects.

In the context of the search for new treatments against AIDS, the processes of adsorption of the virus onto the host cell constitute a particularly attractive therapeutic target due in particular to the fact that this step takes place outside the cell.

Peptides which bind to gp41 and which inhibit its fusion activity have been developed [4, 5]. The clinical studies currently in progress give positive results, indicating that inhibition of the fusion, and therefore of the entry of the virus, effectively corresponds to an advantageous therapeutic target.

As regards the attachment of the virus, various studies have explored the use of soluble CD4 for inhibiting the interaction of the virus with the CD4 expressed at the surface of cells that are targets for HIV. This solution has proved to be ineffective, because, in binding to the virus, the soluble CD4 exposes the CD4i epitope and in fact promotes the interaction of the virus with the CCR5 or CXCR4 coreceptor, which, in certain cases, increases infection [6].

In addition to CD4, the coreceptors are also sites of attachment of the virus to the cells. The natural ligands for these coreceptors are chemikines, in particular RANTES and MIP for CCR5, and SDF for CXCR4. In vitro or on cells in culture, these chemokines inhibit the interaction of the virus with the cells [7, 8], but also induce a certain number of cell responses making them difficult to use from a therapeutic point of view. A certain number of compounds such as AMD301 or peptides which bind to the coreceptors also have antiviral effects [9, 10]. However, in targeting the HIV coreceptors, these various molecules also block the intrinsic functions of the cell linked to the use of these coreceptors.

Besides these cell receptors, HIV is capable of binding to other molecules present on the cells that it infects, such as DC-SIGN, sphingolipids or heparan sulphates [11].

Heparan sulphates are complex polysaccharides belonging to the glycosaminoglycan (GAG) family. They are abundantly present at the cell surface and in interstitial matrices, where they are found anchored to the extracellular domain of specific glycoproteins, heparan sulphate proteoglycans (HSPGs). Heparan sulphates (HSs), which were discovered half a century ago from preparations of heparin (another type of GAG having very similar properties), differ from any other biological macromolecule by virtue of the diversity of their structure and of the functions that they exercise. They are capable in particular of binding HIV gp120, and the virus uses this property in order to adsorb to the surface of target cells. The site of interaction of heparan sulphates on gp120 is located on a variable structure, called V3 loop [12]. However, the exact role of these polysaccharides during infection with HIV remains relatively unclear. Studies have shown that elimination of the heparan sulphates expressed at the surface of cells contributes to making them less permissive to infection with the virus [11], demonstrating the importance of this molecule for the attachment and the entry of the virus.

On the basis of these observations, various polyanionic molecules of the heparin type have been developed in order to inhibit the interaction of the virus with the cells. However, the first clinical trials have shown only little or no activity of these molecules, and it has been possible to observe toxic effects in certain cases [13, 14].

It therefore appears to be necessary to develop new treatments against AIDS that are less restricting, result in fewer side effects and make it possible to avoid evasion of the treatment, i.e. the appearance of resistant viruses which no longer respond to the treatments. It is also necessary to find other anti-HIV therapies that are directed against new targets.

It is in this context that the inventors have produced the present invention.

DISCLOSURE OF THE INVENTION

The aim of the present invention is precisely to overcome the abovementioned disadvantages by providing a novel composition which can be used as an anti-HIV agent. This composition is capable of blocking the entry of the AIDS virus into its host cells. In this respect, it can be used for preparing a medicinal product, in particular a medicinal product intended for the treatment of AIDS.

The composition of the present invention is characterized in that it comprises a polyanion and a molecule capable of inducing the exposure of the CD4i epitope of the gp120 viral protein.

Thus, in accordance with the present invention, the inventors have combined, within a single composition, firstly, a polyanion, for example of the heparin or heparan sulphate type and, secondly, a molecule capable of inducing the exposure of the CD4i epitope of the gp120 viral protein, for example of a soluble CD4 peptide. They have shown that this composition makes it possible to inhibit, unexpectedly, both the virus-cell membrane heparan sulphate interaction, by blocking the V3 loop, and the virus-coreceptor interaction, by blocking the CD4i site. In fact, the inventors have shown that there are actually two domains or sites of interaction of heparin- or heparan sulphate-polyanions on gp120. The first is the V3 loop, the second is the CD4i domain. They have shown (see examples below) that heparin, or heparin fragments of sufficient size, in the presence of a CD4 peptide, interacts with the CD4i domain of the gp120 viral protein and that this combination greatly inhibits the gp120/48d or 17b antibody interaction. 48d or 17b are used as mimics of coreceptors.

This blocking of HIV with the composition of the present invention is all the more unexpected since those skilled in the art are aware that the CD4 molecule used alone can have the reverse effect of that desired, since it exposes the domains for interaction with the coreceptors, and can therefore increase the virus infectivity.

The composition of the present invention is therefore directed towards a novel therapeutic target by means of heparin or other polyanions in the presence of the CD4 peptide, namely the blocking of the interaction of HIV with its coreceptors. This solution is very advantageous, from the therapeutic point of view, for inhibiting the attachment of the virus to the cells, since it targets the virus itself and not the cells. It is therefore, firstly, free of the cellular effects which are observed with the products of the prior art when it is the coreceptors that are targeted. In addition, the toxicity of the composition of the present invention for an organism is less than most of the chemical compounds of the prior art due to the nature of its constituents.

According to the invention, the polyanion may advantageously be chosen from the group consisting of heparin, heparan sulphate, and a polyanion equivalent to heparin or to heparan sulphate. It is, for example, Dextran sulphate (commercial name, Ueno fine chem), Curdlan sulphate (commercial name, Ajinomoto), 2-Naphthalenesulphonate polymer (commercial name, Procept), Pentosan polysulphate (commercial name, Baker norton pharm; Hoechst), or Resobene (commercial name).

The structure of the constituent disaccharide (basic element) of the heparin and of the heparan sulphate according to the present invention is of formula (I) below:

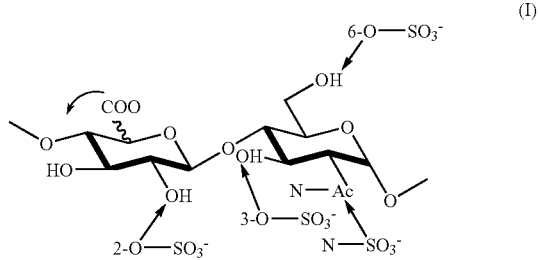

(I)

It is preferable for the polyanion not to be too long, since it would have an anticoagulant activity, which is not desired in the present invention, and would form aspecific bonds with various proteins, in particular thrombin or antithrombin III. Its length will preferably be similar to a heparin chain having a degree of polymerization as defined below. The polyanion preferably has at least two anionic groups per disaccharide. According to the present invention, when the polyanion is heparin or heparan sulphate, it will preferably have a degree of polymerization dp of 10 to 24, advantageously of 12 to 24, preferably of 16 to 22. According to the invention, the heparin, the heparan sulphate or the polyanion equivalent to heparin or heparan sulphate may have a degree of polymerization dp of 12 to 20, for example of 15 to 17.

According to the invention, the polyanion may be prepared by partial depolymerization of heparin or of heparan sulphate by means of an enzymatic method, for example by means of heparinase, or a chemical method, for example by means of nitrous acid. When they are obtained chemically, the heparans may be defined by the presence of N-sulphated or N-acetylated glucosamine, or glucosamine not substituted in the N-position, linked to a uronic acid (glucuronic acid or iduronic acid) with a variable proportion of sulphate group. Structural mimics of these oligosaccharides may be obtained by chemical synthesis.

According to the invention, the molecule capable of inducing the exposure of the CD4i epitope of the gp120 viral protein can be chosen from a CD4 peptide or a derivative of this peptide, or else a monoclonal antibody which binds to the gp120 viral protein and which is capable of activating said gp120 protein in a manner equivalent to the CD4 peptide.

When it is a CD4 peptide, it is preferably soluble for the obvious reasons of facilitation of its interaction with the gp120 viral protein in liquid medium, and of facilitation of its access to its target.

According to the invention, the CD4 peptide advantageously has the sequence (I) below:

(Cys or TPA)-P$^1$Cys-P$^2$Cys-P$^3$Cys-(Ala or Gln)-(Gly or (D)Asp or Ser)-(Ser or His or Asn)-Xaa$^j$Cys-(Thr or Ala)-Cys-Xaa$^k$-NH$_2$     (SEQ ID NO: 19)

in which TPA represents thiopropionic acid, Xaa$^j$ represents β-naphthylalanine, phenylalanine or biphenylalanine, Xaa$^k$ represents Gly, Val or Ileu, P$^1$ represents 3 to 6 amino acids, P$^2$ represents 2 to 4 amino acids and P$^3$ represents 6 to 10 amino acids, the amino acids in P$^1$, P$^2$ and P$^3$ being natural or unnatural, identical or different, and P$^1$, P$^2$ and P$^3$ possibly having a common sequence, said peptide having a β-hairpin conformation in which the β-turn is made up of the amino acid residues Ala or Gln-Gly or DAsp or Ser-Ser or His or Asn-Xaa$^j$ of its sequence (A). In fact, these peptides show a very great affinity for the gp120 viral protein.

Examples of such peptides which can be used in accordance with the present invention are the peptides of sequences ID No. 1 to ID No. 18 of the sequence listing attached in the appendix, or equivalent peptides.

These peptides can be prepared by conventional techniques of solid-phase chemical synthesis or of genetic recombination.

When the molecule capable of inducing the exposure of the CD4i epitope of the gp120 viral protein is an antibody, it can be chosen, for example, from those described in the document Sullivan N, Sun Y, Binley J, Lee J, Barbas C F 3rd, Parren P W, Burton D R, Sodroski J, Determinants of human immunodeficiency virus type 1 envelope glycoprotein activation by soluble CD4 and monoclonal antibodies. *J Virol* 1998; 72(8): pp. 6332-6338.

According to a first embodiment of the present invention, the polyanion and the molecule capable of inducing the exposure of the CD4i epitope of the gp120 viral protein are mixed in said composition. This composition in accordance with the present invention makes it possible to expose the site of interaction with the coreceptors (CD4i site) and, concomitantly, to block this site by means of the oligosaccharide part consisting of the polyanion.

According to this first embodiment, the polyanion and the molecule capable of inducing the exposure of this CD4i epitope of the gp120 viral protein are advantageously mixed in said composition in proportions of 1 to 10 mol of polyanion per 0.5 to 1.5 mol of molecule capable of inducing the exposure of the CD4i epitope of the gp120 viral protein, preferably of 5 mol of polyanion per mole of molecule capable of inducing the exposure of the CD4i epitope of the gp120 viral protein.

The present invention also relates to a method for producing the composition according to this first embodiment of the invention, comprising the following steps:
preparing the polyanion,
preparing the molecule capable of inducing the exposure of the CD4i epitope of the gp120 viral protein,
mixing the polyanion and the molecule capable of inducing the exposure of the CD4i epitope of the gp120 viral protein prepared so as to obtain said composition.

The mixture will preferably be prepared in a biological buffer so that it can be used to produce an administrable medicinal product. The pH is preferably approximately 7, and the solution contains, for example, 15 g/l of NaCl.

According to a second embodiment of the present invention, the polyanion and the molecule capable of inducing the exposure of the CD4i epitope of the gp120 viral protein are linked to one another in said composition. They form a hybrid of polyanion/molecule capable of inducing the exposure of the CD4i epitope of the gp120 viral protein hybrid.

For example, according to the invention, the polyanion and the molecule capable of inducing the exposure of the CD4i epitope of the gp120 viral protein are linked to one another at one of the ends of the polyanion.

When the polyanion used is short, for example with a degree of polymerization dp of 10 to 12, it may be necessary to link the polyanion and the molecule capable of inducing the exposure of the CD4i epitope of the gp120 viral protein by means of a spacer arm, in order to allow the hybrid formed to bind to all its targets on the gp120 viral protein. This may also be the case when the molecule capable of inducing the exposure of the CD4i epitope of the gp120 viral protein is too short. The spacer arm may be any polymer, preferably soluble in aqueous buffers, of appropriate length. Mention may be made, for example, of polyosides or polyglycols. It may be, for example, polyethylene glycol: $(CH_2CH_2O)_n$. Preparations of spacer arms of this type which can be used in the present invention have been widely described in the prior art, for example in documents [18] and [19] (see attached reference list).

The present invention also relates to a method for producing the composition according to the second embodiment of the invention, comprising the following steps:
preparing the polyanion,
preparing the molecule capable of inducing the exposure of the CD4i epitope of the gp120 viral protein,
linking the polyanion and the molecule capable of inducing the exposure of the CD4i epitope of the gp120 viral protein prepared so as to obtain said composition.

The linking of the polyanion with the molecule capable of inducing the exposure of the CD4i epitope can be formed by any techniques known to those skilled in the art, for example for linking a polyanion and a peptide. For example, the various methods described in documents [15], [16] and [17] (see attached reference list) for coupling an oligosaccharide to a polypeptide can be used in the present invention.

According to the present invention, for the reasons mentioned above, it is also possible to use any type of bridging agent, or spacer arm, which binds, firstly, to one end of the oligosaccharide and, secondly, to a part of CD4 that is not essential to its function. The spacer arm may be one of those mentioned above. It can be prepared in the manner described in documents [18] and [19].

The hybrid molecule of the present invention has three advantages: it binds to the gp120 viral protein on the CD4 interaction site, on the V3 loop, when these gp120 molecules are derived from viruses using CXCR4 as coreceptor, and on the domain of interaction with the coreceptors (CD4i domain), as shown diagrammatically in FIG. 7 attached in the appendix. It therefore makes it possible to simultaneously block all the domains that gp120 uses to interact with its cell receptors and coreceptors.

Other characteristics and advantages will become apparent to those skilled in the art in the light of the examples below, given by way of non-limiting illustration, with references to the figures and sequences attached in the appendix.

BRIEF DESCRIPTION OF THE SEQUENCE LISTING

The sequences ID No. 1 to ID No. 18 of the sequence listing attached in the appendix are non-limiting examples of molecules capable of inducing the exposure of the CD4i epitope of the gp120 viral protein for the purpose of the present invention. These molecules are peptides originating from human CD4 (Seq ID No. 1), or artificial peptides originating or derived from scorpion venom peptides (Seq ID Nos. 2 to 18).

EXAMPLES

Figure 1:
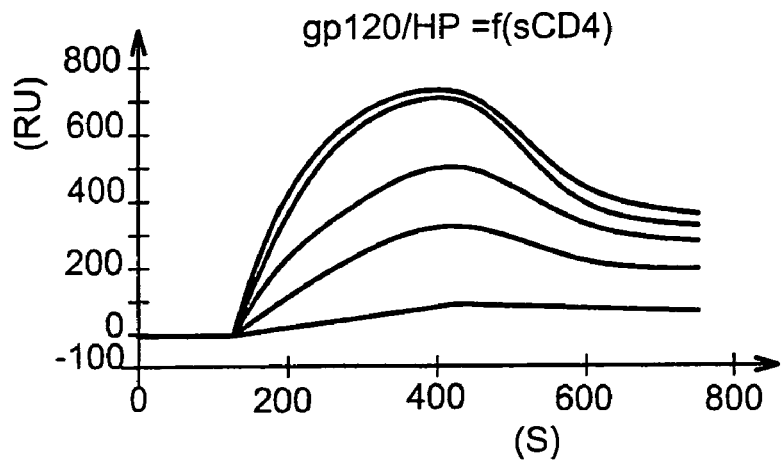
FIG. 1 is a graph representing the amount of gp120/CD4, in resonance units (RU), bound to heparin as a function of time t (in seconds) for various concentrations of CD4 (in nM): curves from bottom to top: 0; 50; 100; 250; 500 nM.

In the following examples, the analyses of gp120-heparin interaction were carried out by surface plasmon resonance (BIAcore system (trademark)). This technique, which makes it possible to perform real-time interaction measurements, also has the advantage of providing a model similar to the physiological reality, where the heparin immobilized on the sensorchip constitutes a two-dimensional interface like the cell surface.

Example 1

Synthesis of a CD4 Peptide which can be used for Producing the Composition of the Present Invention A peptide from a sequence listing attached in the appendix is synthesized by solid-phase chemical synthesis with an Applied Biosystems automatic peptide synthesizer, mod. 433A, and by Fmoc chemistry, which uses the fluorenylmethyloxycarbonyl (Fmoc) group for temporary protection of the α-amino function of the amino acids. The protective groups used to prevent the side reactions of the amino acid side chains, in this Fmoc strategy, were tert-butyl ether (tBu) for the Ser, Thr and Tyr residues; tert-butyl ester (OtBu) for Asp, Glu; trityl (Trt) for Gln, Asn, Cys, His; tert-butyloxycarbonyl (Boc) for Lys and 2,2;5,7,8-pentamethylchroman-6-sulfonyl (Pmc) for Arg.

The coupling reaction takes place with an excess of 10 equivalents of amino acids (1 mmol) relative to the resin (0.1 mmol). The protected amino acid is dissolved in 1 ml of N-methylpyrrolidone (NMP) and 1 ml of a 1 M solution of 1-N-hydroxy-7-azabenzotriazole (HOAt) in the NMP solvent. 1 ml of a 1 M solution of N,N'-dicyclohexylcarbodiimide (DCC) is then added. After activation for 40 to 50 minutes, the active ester formed is transferred into the reactor which contains the resin. Before this transfer then coupling step, the resin is deprotected by removal of its Fmoc group with a 20% solution of piperidine in NMP. The excess piperidine is removed by washing with NMP after approximately 5 to 10 minutes.

After synthesis of the peptide, the peptide-resin is treated five times with a 2% solution of hydrazine in DMF. The coupling of a linker arm is carried out for one hour at ambient temperature in DMF with 10 equivalents of Fmoc-8-amino-3,6-dioxaoctanoic acid using the HBTU reagent in the presence of diisopropyl-ethylamine. The Fmoc group is then deprotected with 20% of piperidine in DMF.

The peptide-resin is immediately treated with 10 equivalents of Traut reagent (2-iminothiolane hydrochloride (Sigma)) in the presence of DIEA. The peptide is finally released and deprotected as described below.

The cleavage of the resin and the cleavage of the protective groups present on the side chains were carried out simultaneously by treating the peptide linked to the resin with trifluoroacetic acid (TFA). Before performing the cleavage, the resin was washed several times with dichloromethane (DCM) and finally dried. The reagent used during the cleavage is an acid mixture containing 81.5% of TFA and phenol scavengers (5%), thioanisol (5%), water (5%), ethanediol (2.5%) and triisopropylsilane (1%). The resin was treated with this mixture for three hours with stirring and at ambient temperature, in a proportion of 100 ml of solution per gram of resin. The free peptide in solution was recovered by filtration. The peptide was then precipitated and washed under cold conditions in diisopropyl ether and then dissolved in 20% acetic acid and lyophilized.

The peptide recovered after lyophilization, the synthesis crude, is in reduced form, i.e. the intrachain disulphide bridges are not formed. The formation of these covalent bonds was performed using the cystamine/cysteamine redox couple. The synthesis crude was taken up in water to which 0.1% (v/v) of TFA and 6 M guanidinium chloride had been added in order to facilitate the dissolving thereof, in a proportion of 2.0 mg·ml$^{-1}$. This solution was then added, dropwise, diluted to 0.2 mg/ml$^{-1}$, to the reducing buffer, made up of 100 mM Tris/HCl, pH 7.8, and 5 mM cysteamine. Cystamine (oxidizing agent), at a final concentration of 0.5 mM, was added after 45 minutes of reaction at ambient temperature. The medium was brought to pH 3.0 after 30 minutes.

The cysteamine makes it possible to reduce the thiol groups present on the peptide. In the open air, it oxidizes and allows the oxidation of cysteines and therefore the folding of the peptide by formation of intrachain disulphide bridges. The cystamine added at the end of the manipulation makes it possible to complete the folding. The correct progress of the oxidation is verified by analytical chromatography, comparing the retention times of the crude and oxidized products, which are greater for the former.

The peptides were purified by reverse-phase high performance liquid chromatography on a Vydac C18 (1.0×25.0 cm) preparative column. A linear gradient of 0-60% acetonitrile in a 0.1% aqueous trifluoroacetic acid solution, over 90 minutes, was used. The fractions of the major peak were analysed by analytical HPLC; the fractions exhibiting just one peak were combined and lyophilized.

The products thus obtained were analysed by mass spectrometry. They are the peptides of the sequence listing attached in the appendix.

Example 2

Synthesis of Polyanion of the Heparin or Heparan Sulphate Type, which can be used for the Composition of the Present Invention A) Enzymatic Synthesis A molecule of heparin or of heparan sulphate having a defined degree of polymerization dp is synthesized.

6 g of heparin are solubilized in a buffer containing 5 mM of Tris, 2 mM of $CaCl_2$, 50 mM of NaCl and 0.1 mg/ml of albumin. The pH is adjusted to 7.5 with acetic acid. This solution is incubated at 25° C. with heparinase I (8 mU/ml) for approximately 50 h (the enzymatic reaction is monitored by means of the increase in optical density, measured at 232 nm).

The mixture is then purified by gel filtration chromatography. The solid phase is Biogel P10, contained in a 1.50 m column 4.4 cm in diameter, eluted at 1 ml/min with 0.25 M NaCl.

Figure 11:
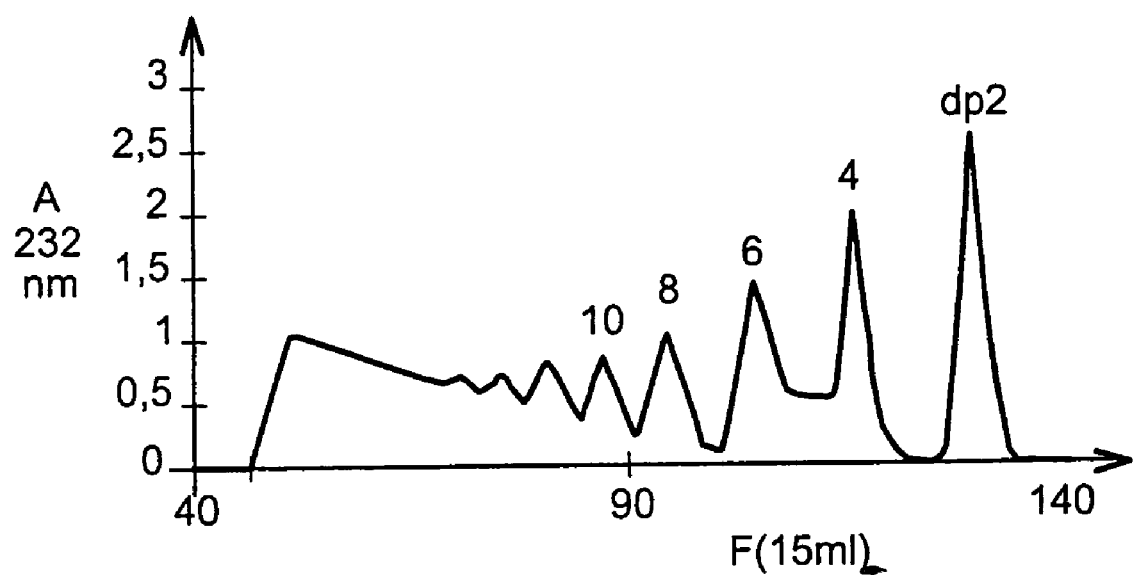
FIG. 11 represents the absorbance at 230 nm of various fractions (F) of 15 ml obtained during an enzymatic synthesis of heparin at degrees of polymerization dp ranging from 2 to 10 (the dp corresponds to the figures indicated on the curve).

FIG. 11 represents the absorbance at 230 nm of the various fractions of 15 ml obtained for degrees of polymerization dp ranging from 2 to 10.

The various oligosaccharides (dp2, dp4, etc.) are dialysed against water and then lyophilized.

B) Synthesis by Chemical Depolymerization from the Natural Product

When the starting material is heparin, the following procedures are carried out: 1 g of heparin is solubilized in 20 ml of sodium nitrite ($NaNO_2$) at 2.1 mg/ml. The solution is adjusted to pH 1.5 with sulphuric acid, and is then incubated at 4° C. for 3 h. The reaction is stopped and the oligosaccharides are purified as above in paragraph A).

When the starting material is heparan sulphate, the following procedure is carried out: 8 g of heparan sulphate are solubilized in 40 ml containing 5 mM of Tris, 2 mM of $CaCl_2$, 50 mM of NaCl and 0.1 mg/ml of albumin. The pH is adjusted to 7.5 with acetic acid. This solution is incubated at 30° C. with heparinase III (25 mU/ml) for approximately 72 h. Heparinase III is again added, for a period of 48 h, and the products are then purified as described above in paragraph A).

Example 3

Synthesis of a Composition of the Present Invention: Mixture of a CD4 Peptide with a Polyanion In this example, a CD4 peptide of Example 1 is mixed with a heparan sulphate prepared in Example 2.

These two molecules are dissolved at a concentration that is two times the desired final concentration. These solubilizations are carried out in a physiological buffer; for example, PBS, TBS (50 mM Tris, 0.15 M NaCl, pH 7.5) or HBS (20 mM Hepes, 0.15 M NaCl, pH 7.5).

The two preparations are then mixed volume for volume (1/1).

Example 4

Synthesis of a Composition of the Present Invention: Coupling of a CD4 Peptide with a Polyanion In this example, a CD4 peptide of Example 1 is coupled with the heparan sulphate prepared in Example 2.

The heparan sulphate is incubated with a molar excess of hydrazine or of carbodihydrazide. The function of this step is to place a hydrazine group on the reductive end of the oligosaccharide, when it is prepared by enzymatic depolymerization, or on the aldehyde of the oligosaccharide, when it is prepared by chemical depolymerization with nitrous acid.

The carbohydrates of the soluble CD4 peptide are oxidized by treatment with sodium periodate, and the aldehyde function thus created is used for the coupling of the hydrazine-containing oligosaccharide.

The oligosaccharide, generally in solution at 1 mM in PBS buffer (sodium phosphate saline), is coincubated with a molar excess (for example up to 100 times) of hydrazine or of carbodihydrazide, also in solution in PBS. The reaction mixture is incubated at ambient temperature, then purified by desalification or dialysis against distilled water and, finally, dried by evaporation under vacuum or lyophilized.

The glycosylated (produced in mammalian cells or insect cells) soluble CD4 molecule (sCD4) is taken up in a 20 mM phosphate buffer, pH 6.2, and then treated with sodium periodate (10 mM) for 20 minutes at 4° C. and in the dark. To remove the sodium periodate, the reaction mixture is desalified by gel filtration or by dialysis against the phosphate buffer.

The sCD4, the glycans of which are thus oxidized, is coincubated with a molar excess of hydrazine-containing oligosaccharide at 4° C., so as to form a complex between the two molecules.

When the CD4 is not glycosylated, the procedure is carried out in the manner described by Najjam et al., in document [17].

It is also possible to use any type of bridging agent which binds, firstly, to one end of the oligosaccharide and, secondly, to a part of the CD4 peptide that is not essential to its function.

Those skilled in the art will have no difficulty in implementing this process or an equivalent process.

Example 5

Demonstration of the Increase in the Affinity of gp120 for Heparin by Means of CD4

30 resonance units (RU) of biotinylated heparin are immobilized at the surface of a biochip ("sensorchip" B1 produced by the company Biacore).

gp120 (hxbc2) at 50 nM is incubated for 1 hour 30 min with increasing concentrations of soluble CD4 at 0, 50, 100, 250 or 500 nM, and then injected onto the heparin surface at 10 µl/min.

The analyses of gp120-heparin interaction by surface plasmon resonance were carried out as a function of time.

The curves in FIG. 1 correspond to the injection of gp120 at 50 nM and of CD4 respectively at 0, 50, 100, 250 or 500 nM (respectively for the curves from bottom to top in this figure).

Figure 2:
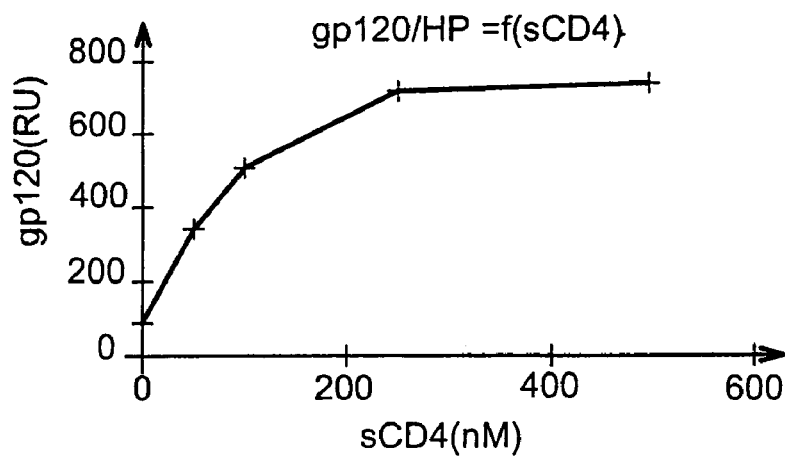
FIG. 2 is a graph representing the amount of gp120/CD4, in resonance units (RU), bound to heparin as a function of the concentration of CD4 (in nM).

FIG. 2 shows the amount of gp120/CD4 bound to the heparin as a function of the concentration of CD4.

It appears that a CD4:gp120 molar ratio of approximately 5:1 produces the maximum response.

These results show that exposure of the CD4i domain of gp120 greatly increases the interaction of gp120 with heparin. CD4i therefore represents a new site of interaction with heparin.

Example 6

CD4-Dependent gp120/48D Interaction

1250 RU of antibody 48d specific for the CD4i epitope are immobilized at the surface of a biochip ("sensorchip" B1) as in Example 1 above.

The gp120 viral protein (hxbc2) at 50 nM is incubated for 1 h 20 min with increasing concentrations of soluble CD4 at 0, 50, 100, 240 or 500 nM, and then injected onto the 48d surface at 10 µl/min.

The analyses of gp120-heparin interaction by surface plasmon resonance were carried out as a function of time.

Figure 3:
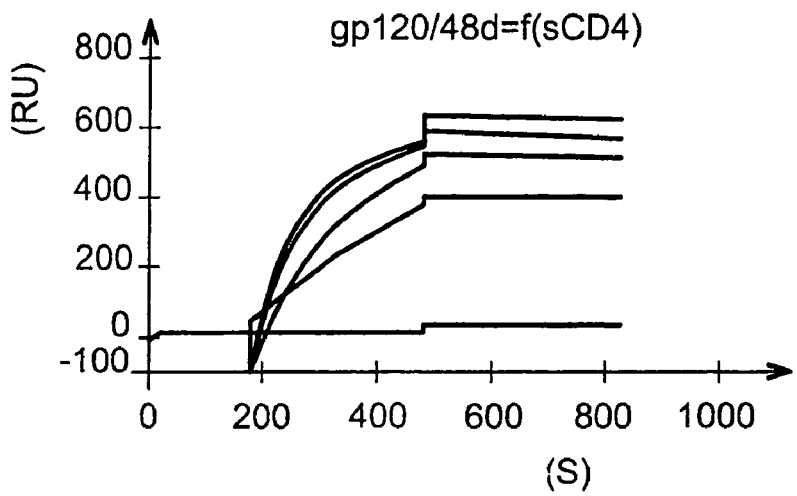
FIG. 3 is a graph representing the evolution of the gp120 viral protein/antibody 48d interaction (response RU) as a function of time (in seconds) for various concentrations of CD4 peptide (in nM): curves from bottom to top: 0; 50; 100; 250; 500 nM.

The curves in FIG. 3 correspond to the injection of gp120 at 50 mM and of CD4 respectively at 0, 50, 100, 250 or 500 nM (respectively for the curves from bottom to top in this figure).

This example shows that the gp120/48d interaction is CD4-dependent, and that 48d interacts with CD4i, the coreceptor recognition domain. This antibody can therefore be used as a model for the interaction of gp120 with a coreceptor.

Example 7

Inhibition of the gp120 Protein-48d Interaction by Heparin

The gp120 protein is coincubated for 40 minutes with CD4. The mixture is then divided up into 5 aliquots, to which the heparin (15 kDa) is added at various concentrations.

The final concentrations in the aliquots are: gp120:50 nM; CD4:250 nM and heparin: 0, 3, 6, 12 or 30 µg/ml, respectively, from top to bottom in FIG. 4. On the top curve, where there is no heparin, the gp120/CD4 interaction is visualized; all the other curves are in the presence of heparin (from 3 to 30 µg/ml, respectively, from top to bottom, FIG. 4).

After incubation for 40 minutes, the various mixtures are injected onto the 48d surface.

The analyses of gp120-heparin interaction by surface plasmon resonance were carried out as a function of time.

Figure 4:
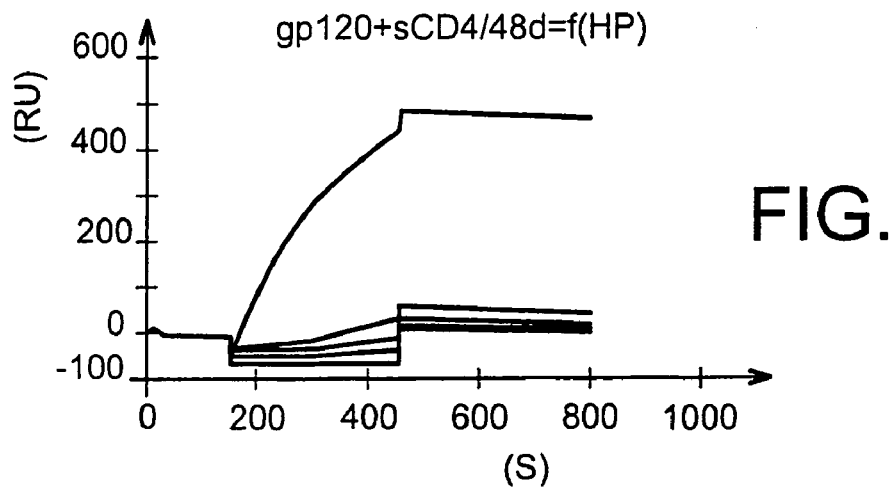
FIG. 4 is a graph representing the inhibition of the interaction of the gp120/CD4 complex with the antibody 48d (response RU) as a function of time (in seconds) by various concentrations of heparin H (in nM): curves from top to bottom: 0; 3; 6; 12; 30 µg/ml.

The results obtained are represented in FIG. 4. They show that heparin inhibits the adsorption of the gp120/CD4 complex onto the 48d-antibody surface. The heparin is, moreover, found to be an effective inhibitor since the inhibition is virtually complete from the lowest of the concentrations tested (3 µg/ml).

This shows that the heparin competes with 48d and therefore binds to CD4i.

This example indicates that the inhibitory activity of the oligosaccharides (heparin), as defined above, is obtained in the presence of CD4.

This result makes it possible to propose the use of a hybrid molecule made up of CD4 and of oligosaccharides of the heparin type, linked covalently, or of a mixture of these two molecules.

The direct interaction of the CD4i domain with a polyanion has never been described in the prior art, neither has inhibition of the gp120-antibody 48d interaction by a polyanion. No studies existed showing the possible inhibition of gp120 with the coreceptors by means of a molecule of the heparin type.

Example 8

Inhibition of the gp120-48d Interaction with Oligosaccharide Fragments of Defined Sizes The oligosaccharide fragments of defined sizes are obtained by enzymatic depolymerization.

The gp120 viral protein is coincubated for 60 minutes with CD4 so as to expose the CD4i domain. The mixture is divided up into 8 aliquots and heparin fragments of increasing size, comprising from 1 to 8 basic disaccharide units, i.e. a degree of polymerization (dp) of 2 to 16, are added so as to give final concentrations of 50 nM for gp120, 250 nM for CD4 and 125 nM for the heparin fragments (the molecular mass of a disaccharide is approximately 600 Da).

Figure 5:
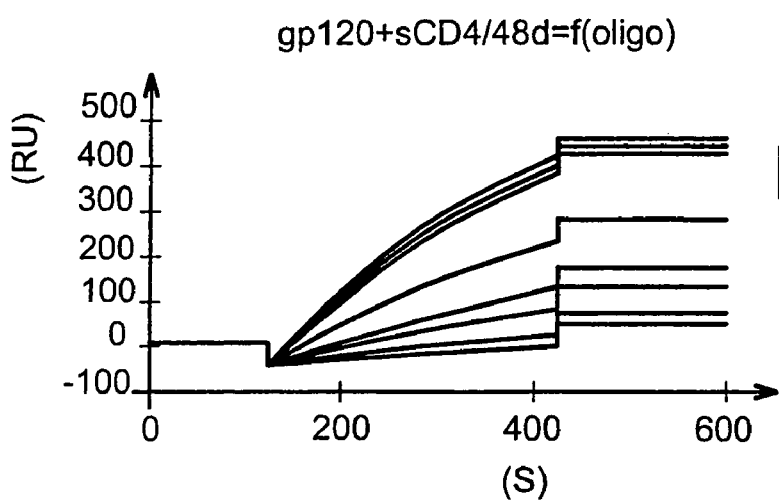
FIG. 5 is a graph representing the inhibition of the amount of gp120/CD4 complexes bound to 48d as a function of the size of the heparin fragment in degree of polymerization, from dp 0 to dp 18 (curves from top to bottom: dp 0; dp 2; dp 4; dp 6; dp 8; dp 10; dp 12; dp 14; dp 16; dp 18).
Figure 6:
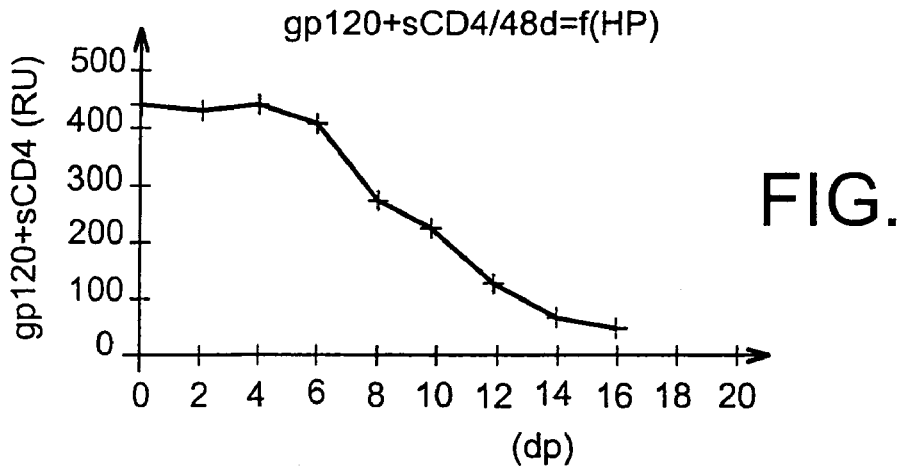
FIG. 6 is a graph representing the amount of gp120/CD4 complexes bound to 48d as a function of the size of the heparin fragment based on the data represented in FIG. 5.
Figure 7:
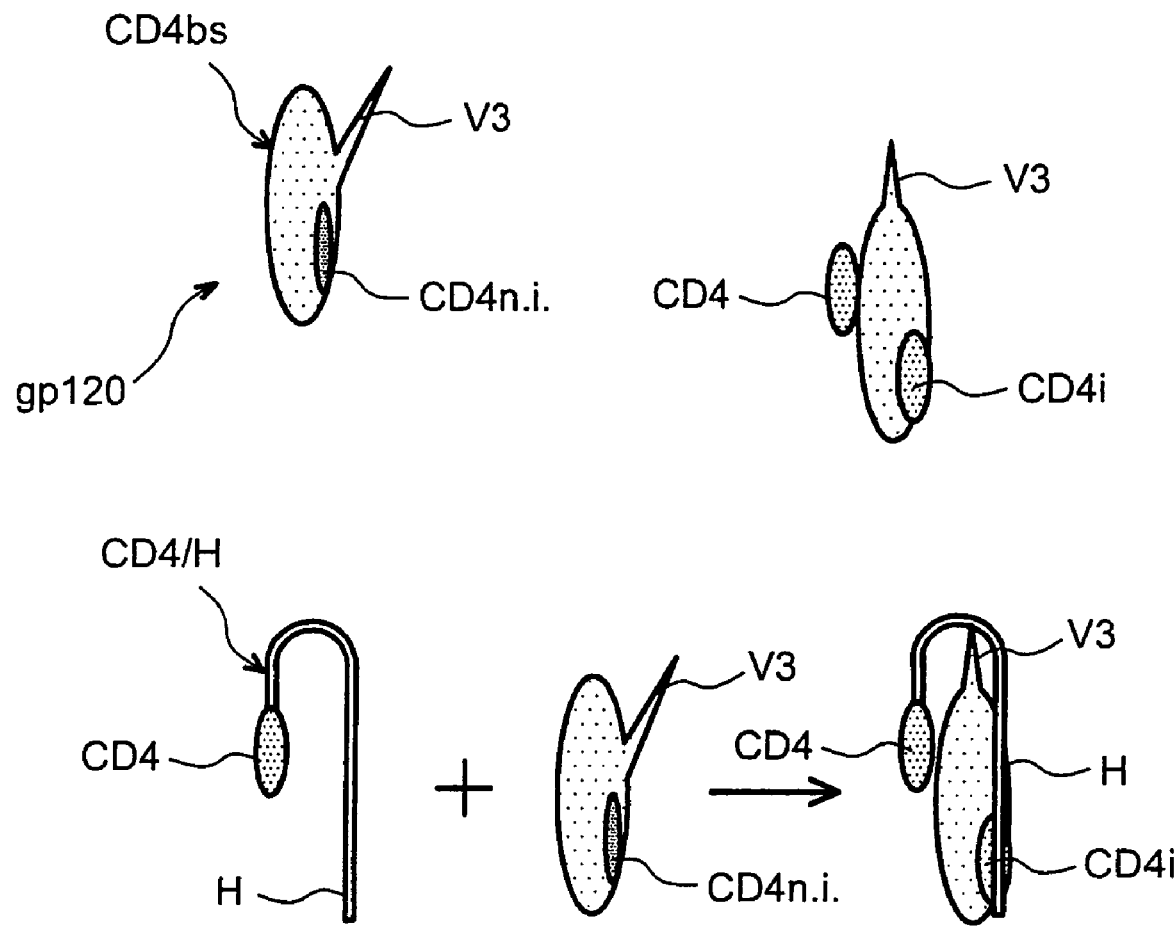
FIG. 7 is a drawing showing diagrammatically the gp120 viral protein, and the interaction of a composition in accordance with the second embodiment of the present invention with the gp120 viral protein. In this figure, sCD4bs ("s" for soluble, "bs" for binding site)=CD4-binding site, V3=V3 loop, CD4ni=non-induced ("ni"), (non-accessible) coreceptor-binding site, CD4i=coreceptor-binding site induced by the binding of CD4 to gp120 ("i" for induced), CD4/H=hybrid molecule of CD4 peptide/heparin or heparan sulphate according to the second embodiment of the present invention, and H=heparin or heparan sulphate.
Figure 8:
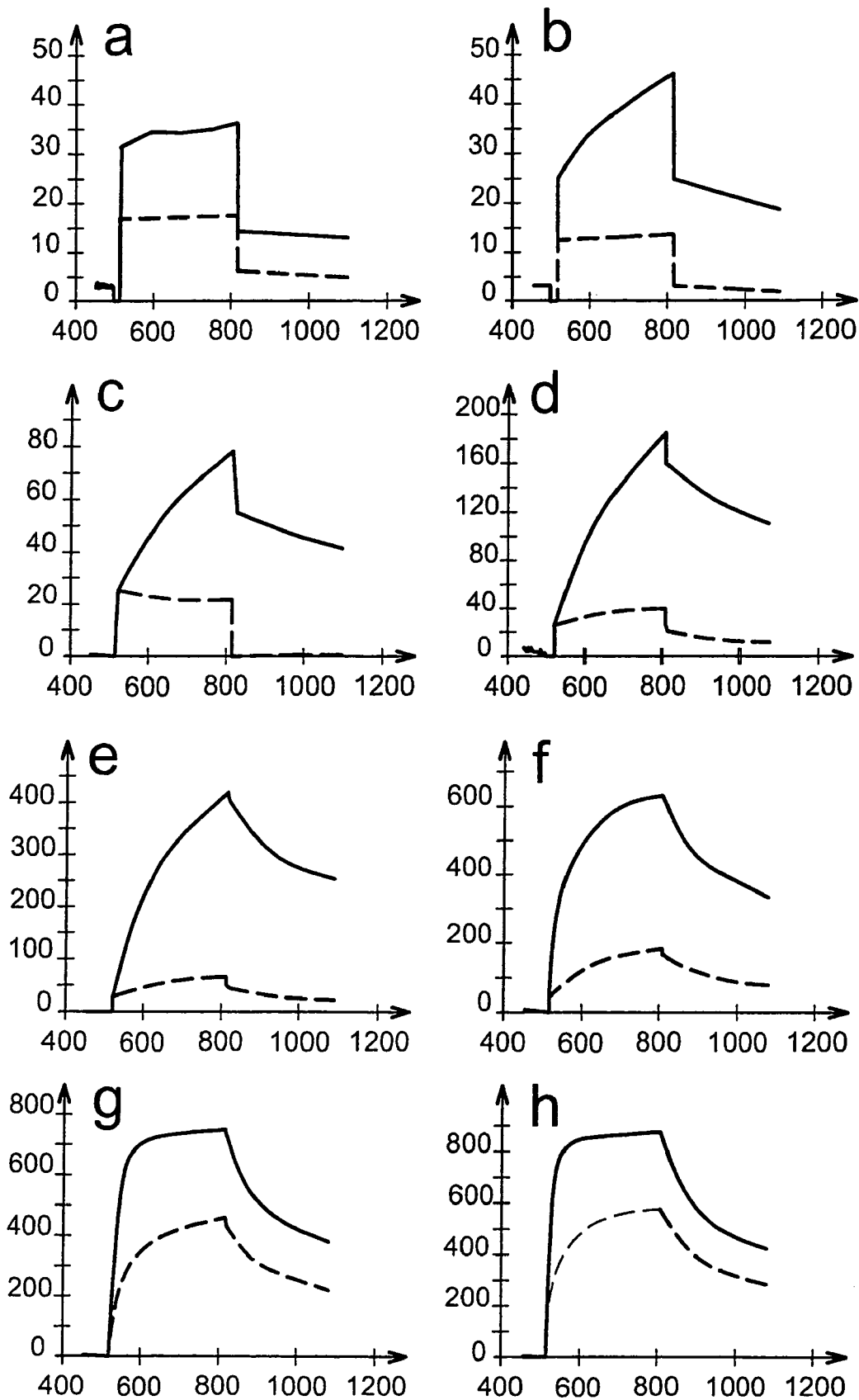
FIGS. 8 a) to h) are representations in the form of graphs of the interaction of complexes of gp120 viral protein and gp120/CD4 on an activated sensorchip with heparin, at various concentrations of gp120 viral protein: 0 nM (a); 0.62 nM (b); 1.25 nM (c); 2.5 nM (d); 5 nM (e); 10 nM (f), 20 nM (g) and 40 nM (h), with preincubation (continuous lines) or without preincubation (discontinuous lines) with 80 nM of soluble CD4.
Figure 9:
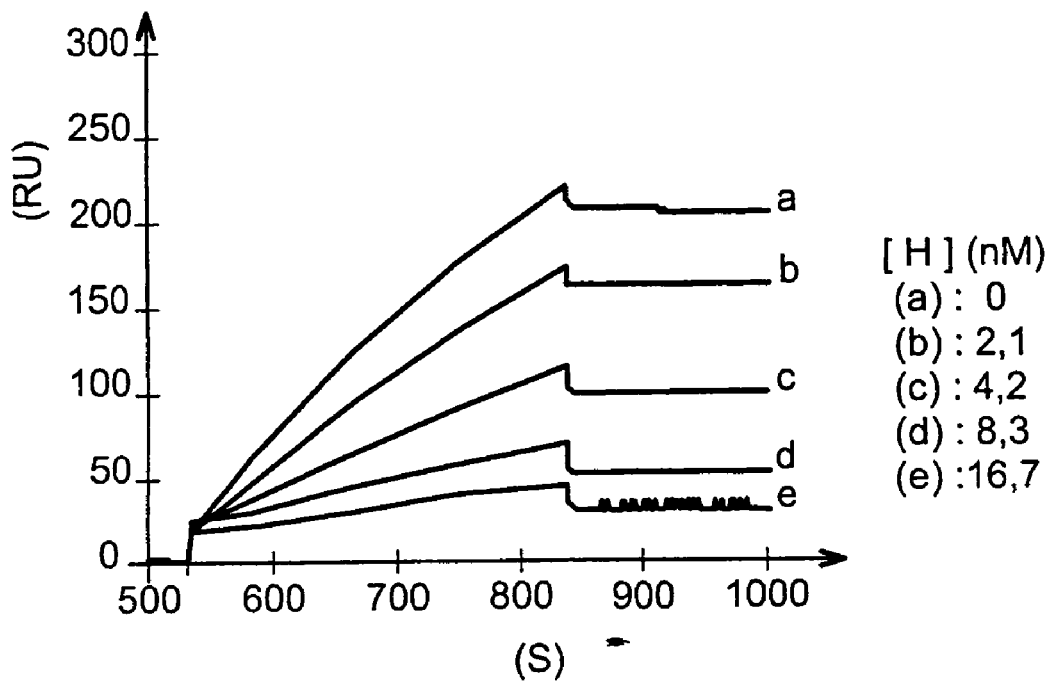
FIG. 9 is a representation in the form of a graph of the inhibition of the gp120/CD4 interaction by heparin and oligosaccharides of heparin (H) on a sensorchip activated with mAb17b. The gp120 viral protein (5 nM) was preincubated successively with a CD4 peptide (10 nM) and with concentrations of heparin ([H]) at 0 nM (curve a); 2.1 nM (b); 4.2 nM (c); 8.3 nM (d); and 16.7 nM (e), before being injected onto the mAb17b surface.
Figure 10:
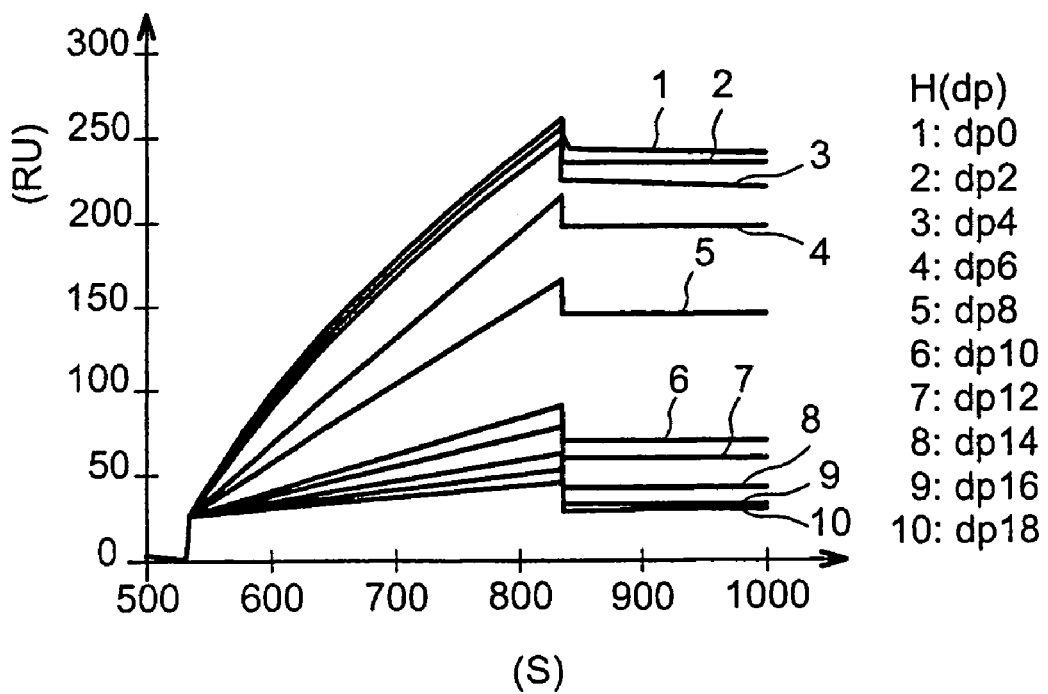
FIG. 10 is a representation in the form of a graph of the inhibition of the gp120/CD4 interaction by heparin and oligosaccharides of heparin (H) on the sensorchip activated with mAb17b. The gp120 viral protein (5 nM) was preincubated successively with a CD4 peptide (10 nM) and with a concentration of heparin of 40 nM, with various degrees of polymerization: dp 0 (curve 1); dp 2 (curve 2); dp 4 (curve 3); dp 6 (curve 4); dp 8 (curve 5); dp 10 (curve 6); dp 12 (curve 7), dp 14 (curve 8); dp 16 (curve 9); dp 18 (curve 10), before being injected onto the mAb17b surface.

The mixtures are then injected onto the 48d surface (FIG. 5). The data obtained make it possible to represent the amount of gp120/CD4 complexes bound to 48d as a function of the size of the heparin fragment (FIG. 6).

These results show that oligosaccharides of size equal to or less than dp6 (3 disaccharides) do not have the ability to block the interaction of the gp120/CD4 complex with 48d.

On the other hand, the interaction is completely inhibited by the fragments whose size is greater than dp10, and better still greater than dp12, at the concentration tested.

These results reveal, for example, that a concentration of 125 nM of heparin having a degree of polymerization equal to 16 (dp16), i.e. 0.6 µg/ml, in the presence of CD4 at 250 nM, inhibits 90 to 100% of the interaction of the 48d antibody with gp120 (50 nM), which confirms the existence of a direct interaction. Similarly, oligosaccharides of heparin of type dp14 to dp18 at 40 nM inhibit the interaction of the gp120 (5 nM)/CD4 (10 nM) complex with 17b antibody.

These results show that heparin, a molecule having a structure very similar to heparan sulphates, also interacts with a second binding site on gp120. This site, called CD4i, is an epitope that is only exposed when gp120 interacts with CD4, which constitutes the HIV coreceptor binding site. These results show that the presence of CD4, the effect of which is to expose the CD4i site, very substantially increases the gp120-heparin or gp120-heparan sulphate interaction; this has never been described elsewhere and constitutes the first proof of a possible interaction between gp120 and heparin or heparan sulphate via the CD4i site.

A molecular modelling study showed that the CD4i site of gp120 consists of basic amino acids. These basic amino acids are aligned on the surface of the protein, and effectively constitute a site for interaction with heparin, or oligosaccharides derived from heparin or from heparan sulphate.

The inventors therefore hereby propose a therapeutic use of the polyanionic compounds targeting this novel site of interaction. The approach consists of the conjugated use of polyanions and of molecules capable of exposing the CD4i epitope, by coadministration or in the form of a hybrid molecule. This type of molecule simultaneously blocks all the domains of interaction of gp120 with the host cells.

Example 9

Protocol for the Activation of Oligosaccharides for the Purpose of Coupling them with a Protein The protocol is based on the reaction of an aldehyde group (on the oligosaccharide) with an amine or hydrazide group on the protein.

When the oligosaccharides are obtained by chemical depolymerization of heparin (with nitrous acid), the aldehyde function is created at the cleavage site and the oligosaccharide is ready for the coupling.

When the oligosaccharides are obtained by enzymatic depolymerization, the following procedure may be carried out:

The oligosaccharides, at a concentration of approximately 10 mM, are incubated in a saturating solution of ammonium bicarbonate for 96 hours. The reaction mixture is then purified on a gel filtration column, equilibrated with 10 mM ammonium bicarbonate, and the sample is then lyophilized several times in order to eliminate the residual ammonium bicarbonate. The aim of this step is to create a glycosylamine at the reductive end of the oligosaccharide.

Alternatively, the oligosaccharide (10 mM) may also be incubated with 0.25 mM of dihydrazide adipate, in the presence of sodium cyanoborohydride ($NaBH_3CN$, 1 M) at pH 5, for 96 hours. The reaction mixture is then purified on a gel filtration column, equilibrated in distilled water, and then dried by lyophilization. The aim of this step is to introduce a hydrazide function at the reductive end of the oligosaccharide.

The oligosaccharides, prepared according to the two methods above, are then incubated with 0.5 M of diglutyraldehyde, at pH 5, for 4 hours, and then with 0.1 M of $NaBH_3CN$ for 30 minutes. The reaction mixture is then purified on a gel filtration column, equilibrated in distilled water, and then dried by lyophilization. The aim of this step is to place an aldehyde function at the reductive end of the oligosaccharides.

Example 10

Demonstration of the Inhibitory Activity of the Oligosaccharides on the Interaction of GP120 with the Coreceptor (CXCR4) for the Virus CHO cells (mutant 2241, deficient in glycosaminoglycan expression, they do not produce heparan sulphate) transfected with the CXCR4 gene are preincubated with: gp120 (20 µg/ml), with or without heparin, or gp120/CD4 complexes (20 µg/ml for each of the proteins), or gp120/CD4 complexes incubated beforehand with 6 kDa heparin (10 µg/ml) or a heparin dodecasaccharide (10 µg/ml).

The gp120 bound to the surface of the cells is detected using an anti-gp120 antibody coupled to an FITC-labelled secondary antibody, and then analysed by FACS.

Figure 12:
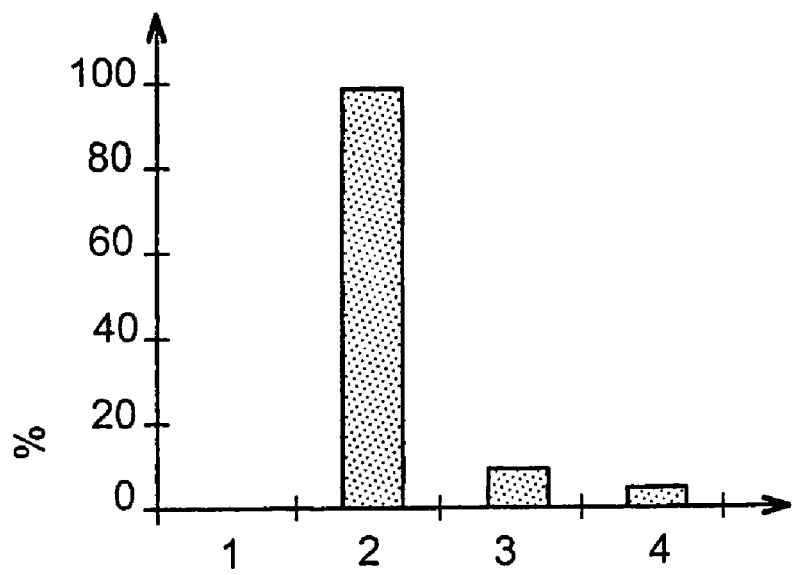
FIG. 12 is a graph produced from the experimental results of Example 10. This graph shows the percentages of gp120/CXCR4 interaction in the presence or absence of heparin.

The results represented in FIG. 12 attached in the appendix show the percentages of gp120/CXCR4 interaction. The negative control (0%) corresponds to the non-specific binding of gp120 to the cells (gp120 alone or in the presence of heparin) (1). The positive control (100%) is observed for the gp120/CD4 complexes (2), and corresponds to the binding of gp120 to the CXCR4 coreceptor, induced by CD4. The heparin (3) and the dodecasaccharide (4) both greatly decrease the interaction (8.5 and 4.1%, respectively, i.e. 91.5 and 95.9% inhibition).

The heparin used clearly inhibits the interaction of gp120 with the coreceptor.

BIBLIOGRAPHICAL REFERENCES

[1] Chan D. C., Kim P. S. (1998) HIV entry and its inhibition. *Cell* 93:681-684.

[2] Claphan P. R. 1997 HIV and chemokines: ligands sharing cell-surface receptors. *Trends in cell biol.* 7:264-268.

[3] Michael N. L., Moore J. P. (1999), HIV entry inhibitors: evading the tissue, *Nat Med* 5:740-2.

[4] Chan D. C., Chutkowski C. T., Kim P. S. (1998), Evidence that a prominent cavity in the coil of HIV type 1 gp41 is an attractive drug target, *Proc Natl Acad Sci USA* 95:15613-7.

[5] Doms R. W., Moore J. P. (2000), HIV-1 membrane fusion: targets of opportunity. *J. Cell Biol* 151:F9-14.

[6] Schenten D., Marcon L., Karlsson G. B., Parolin C., Kodama T., Gerard N., Sodroski J. (1999), Effect of soluble CD4 on simian immunodeficiency virus infection of Cd4-positive and CD4-negative cells, *J. Virol.* 73:5373-80.

[7] Chen J. D., Bai X., Yang A. G., Cong Y., Chen S. Y. (1997), Inactivation of HIV-1 chemokine co-receptor CXCR-4 by a novel intrakine strategy. *Nat Med* 3:1110-6.

[8] Oberlin E., Amara A., Bachelerie F., Bessia C., Virelizier J. L., Arenza-Seisdedos F., Schwartz O., Heard J. M., Clark-Lewis I., Legler D. F., Loetscher M., Baggiolini M., Moser B., (1996), The CXC chemokine SDF-1 is the ligand for LESTR/fusion and prevent infection by T-cell-line-adapted HIV-1. Nature 382:833-5.

[9] Proudfoot A. E., Wells T. N., Clapham P. R., (1999) Chemokine receptors-future therapeutic targets for HIV? *Biochem Pharmacol.* 57:451-63.

[10] Murakami T., Nakajima T., Koyanagi Y., Tachibana K., Fujii N., Tamamura H., Yoshida N., Waki M., Matsumoto A., Yoshie O., Kishimoto T., Yamamoto N., Nagasawa T., (1997), A small molecule CXCR4 inhibitor that blocks T cell line-tropic HIV-1 infection. *J. Exp Med* 186:1389-93.

[11] Mondor I., Ugolini S., Sattentau Q. J., (1998): "Human Immunodeficiency Virus Type 1 Attachment to HeLa CD4 Cells Is Independent and gp120 Dependent and Requires Cell Surface Heparans", *J. Virol.* 72:3623-34.

[12] Roderiquez G., Oravecz T., Yanagishita M., Bou-Habib D. C., Mostowski H., Norcross M. A., (1995): "Mediation of human immunodeficiency virus type 1 binding by interactions of cell surface heparan sulphate proteoglycans with the V3 region of envelope gp120-gp41", *J. Virol.* 69:2233-9.

[13] Abrams D. I., Kuno S., Wong R., Jeffords K., Nash M., Molaghan J. B., Gorter R., Uenor R., (1989): "Oral dextran sulfate (UA001) in the treatment of the acquired immunodeficiency syndrome (AIDS) and AIDS-related complex". *Ann. Intern. Med.* 110:183-8.

[14] Flexner C., Barditch-Crovo P. A., Kornhauser D. M., Farzadegan H., Nerhood L. J., Chaisson R. E., Bell K. M., Lorentsen K. J., Hendrix C. W., Petty B. G., Lietman P. S., (1991): Pharmacokinetics, toxicity, and activity of intravenous dextran sulfate in human immunodeficiency virus infection", *Antimicrob. Agents Chemother.* 335:2544-50.

[15] Chernyak A., Karavanov A., Ogawa Y., Kovac P., Conjugating oligosaccharides to proteins by squaric acid diester chemistry: rapid monitoring of the progress of conjugation, and recovery of the unused ligand, *Carbohydr. Res.* 2001, 330(4):479-486.

[16] Kuberan B., Gunay N. S., Dordick J. S., Linhardt R. J., Preparation and isolation of neoglycoconjugates using biotin-streptavidin complexes, *Glycoconj. J* 1999, 16(6): 271-281.

[17] Najjam S., Gibbs R. V., Gordon M. Y., Rider C. C., Characterization of human recombinant interleukin 2 binding to heparin and heparan sulfate using an ELISA approach, *Cytokine* 1997, 9(12):1013-1022.

[18] Dreef-Tromp C. M., Basten J. E., Broekhoven M. A., Van Dinther T. G., Petitou M., Van Boeckel C. A., Biological properties of synthetic glycoconjugate mimics of heparin comprising different molecular spacers, *Bioorg. Med. Chem. Lett.* 1998, 8-16:2081-2086.

[19] Grootenhuis P. D., Westerduin P., Meuleman D., Petitou M., Van Boeckel C. A., Rational design of synthetic heparin analogues with tailor-made coagulation factor inhibitor activity, *Nat. Struct. Biol.* 1995, 2(9):736-739.

---

The invention claimed is:

1. A composition comprising:
   a polyanion selected from the group consisting of heparin, heparan sulphate, and a polyanion equivalent to heparin or heparan sulphate selected from the group consisting of dextran sulphate, curdian sulphate, 2-naphthalene sulphonate polymer, pentosan polysulphate and resobene, said polyanion having a degree of polymerization dp of 10 to 24, and
   a CD4 peptide of according to formula (I):

(Cys or TPA)-$P^1$-Cys-$P^2$-Cys-$P^3$-Cys-(Ala or Gln)-
   (Gly or (D)Asp or Ser)-(Ser or His or Asn)-$Xaa^j$-
   Cys-(Thr or Ala)-Cys-$Xaa^k$-$NH_2$           (I)

wherein TPA represents thiopropionic acid, $Xaa^j$ represents β-naphthylalanine or biphenylalanine, $Xaa^k$ represents Gly, Val or Ile, $P^1$ represents 3 to 6 amino acids, $P^2$ represents 2 to 4 amino acids and $P^3$ represents 6 to 10 amino acids, the amino acids in $P^1$, $P^2$ and $P^3$ being natural or unnatural, identical or different, and $P^1$, $P^2$ and $P^3$ optionally having a common sequence, said CD4 peptide sequence according to formula (I) having a β-hairpin conformation wherein the β-turn comprises the amino acid residues (Ala or Gln)-(Gly or (D)Asp or Ser)-(Ser or His or Asn)-$Xaa^j$.

2. The composition according to claim 1, wherein said polyanion has a degree of polymerization dp of 12 to 20.

3. The composition according to claim 1, wherein said polyanion has a degree of polymerization dp of 15 to 17.

4. The composition according to claim 1, wherein the CD4 peptide according to formula (I) is selected from group consisting of SEQ ID NO:5, SEQ ID NO:10, SEQ ID NO:11, SEQ ID NO:12, SEQ ID NO:13 and SEQ ID NO:14.

5. The composition according to claim 1, wherein the composition comprises 1 to 10 mol of polyanion per 0.5 to 1.5 mol of the CD4 peptide according to formula (I).

6. The composition according to claim 1, wherein the composition comprises 5 mol of polyanion per mole of the CD4 peptide according to formula (I).

7. An anti-HIV composition comprising the composition according to claim 1.

* * * * *